United States Patent
Harreld et al.

(10) Patent No.: US 6,500,142 B1
(45) Date of Patent: Dec. 31, 2002

(54) COVERED SUCTION DEVICE WITH CLOSURE

(75) Inventors: Donald R. Harreld, Woodstock, IL (US); Richard A. Rude, Crystal Lake, IL (US); Edward C. Hay, Crystal Lake, IL (US)

(73) Assignee: Sage Products, Inc., Crystal Lake, IL (US)

( * ) Notice: Subject to any disclaimer, the term of this patent is extended or adjusted under 35 U.S.C. 154(b) by 92 days.

(21) Appl. No.: 09/679,166

(22) Filed: Oct. 4, 2000

(51) Int. Cl.[7] .................................................. A61M 1/00
(52) U.S. Cl. ......................................................... 604/35
(58) Field of Search ........................... 604/48, 35, 523, 604/315, 198, 263, 162, 164.08, 167.01, 167.02, 192, 93.01, 264

(56) References Cited

U.S. PATENT DOCUMENTS

| | | | |
|---|---|---|---|
| 4,691,702 A | | 9/1987 | Chantzis ................ 128/207.16 |
| 5,334,149 A | * | 8/1994 | Nortman et al. ............. 604/110 |
| 5,406,939 A | | 4/1995 | Bala ............................... 128/4 |
| 5,527,297 A | | 6/1996 | Paul ............................ 604/263 |
| 5,569,202 A | | 10/1996 | Kovalic ....................... 604/110 |
| 5,695,474 A | | 12/1997 | Daugherty ................... 604/162 |
| 5,904,699 A | | 5/1999 | Schwemberger ............ 606/185 |

* cited by examiner

*Primary Examiner*—Anhtuan T. Nguyen
*Assistant Examiner*—Ann Y. Lam
(74) *Attorney, Agent, or Firm*—Lee, Mann, Smith, McWilliams, Sweeney & Ohlson

(57) ABSTRACT

A suction device which can be protected after use. The suction device includes an elongated suction tube having a suction tip at one end. A retractable, protective sheath is connected to the tube and extendable over the exposed length of the suction tube. A closure is secured to the free end of the sheath, and includes a cap which can be pivoted to a closed position. So as to avoid contamination, an automatic closer is provided to pivot the cap to the closed position.

20 Claims, 2 Drawing Sheets

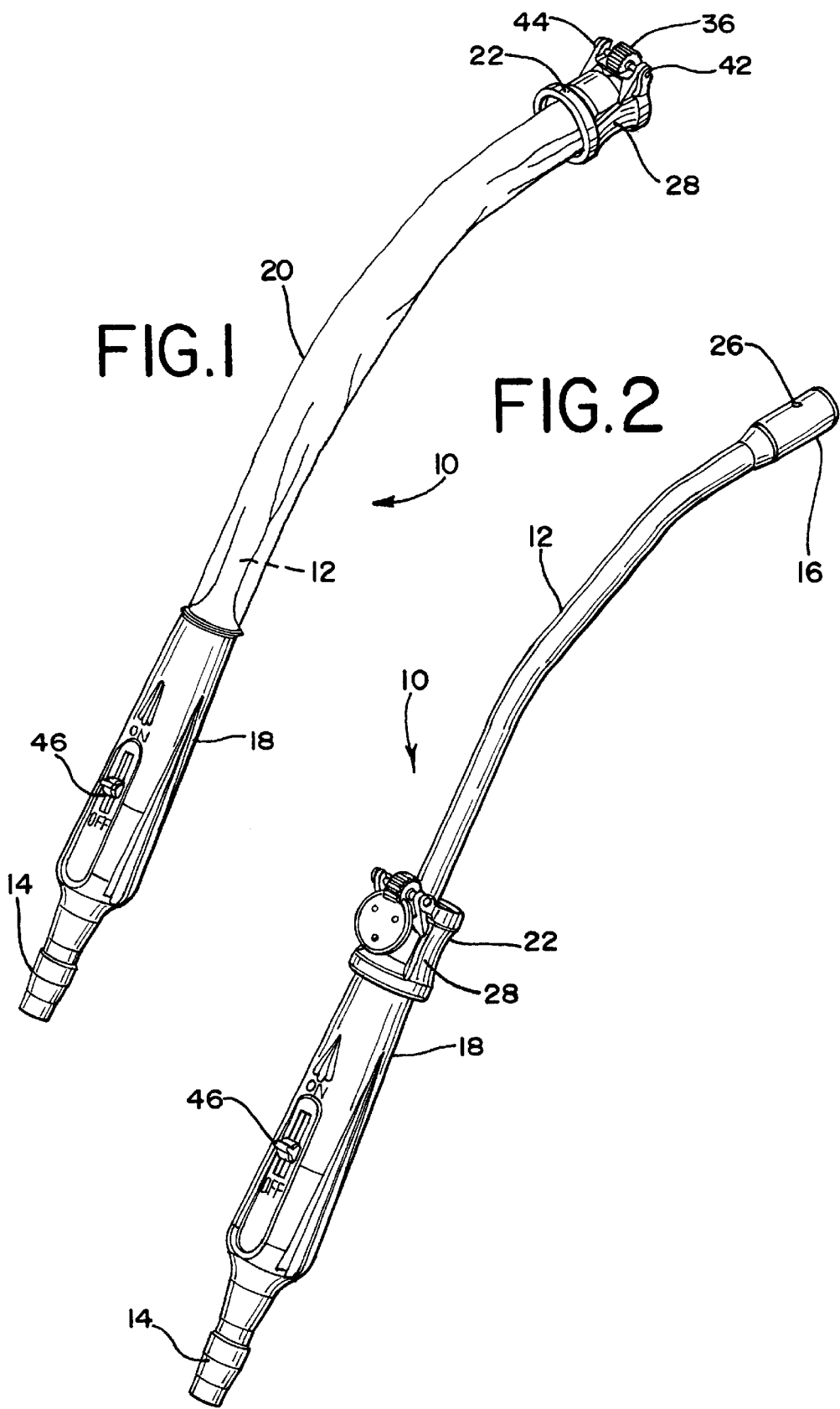

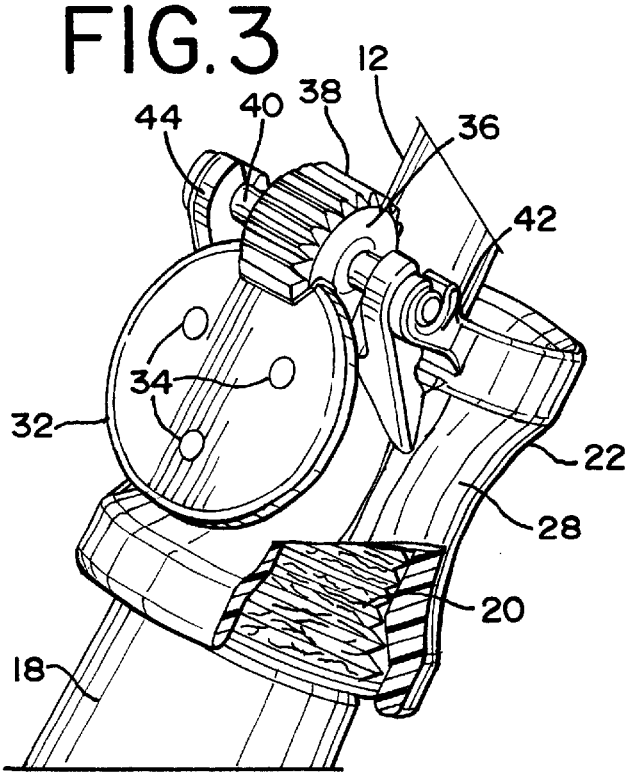
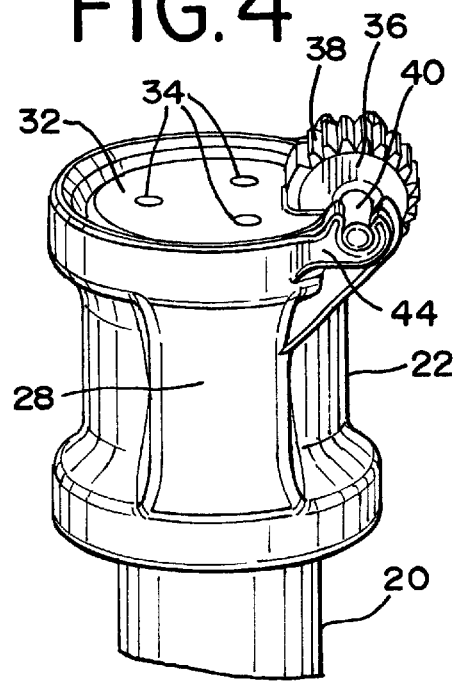
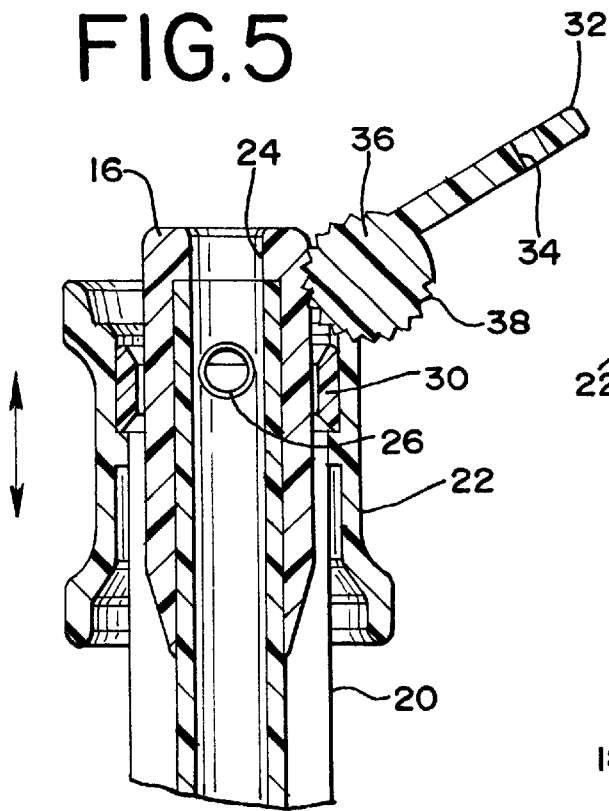
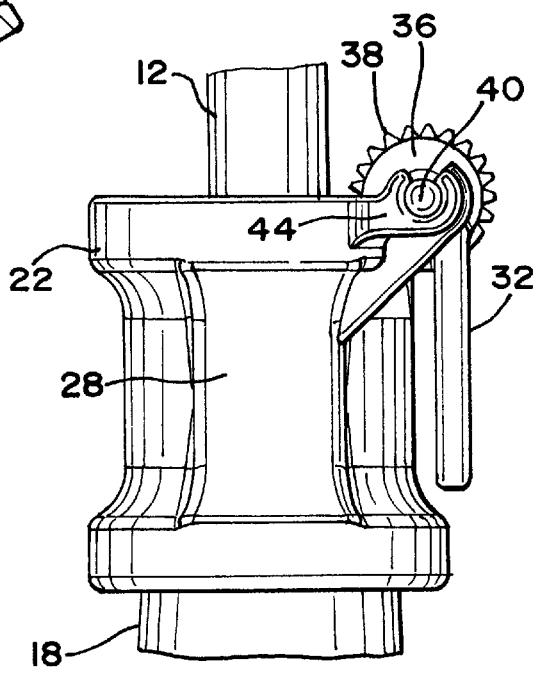

COVERED SUCTION DEVICE WITH CLOSURE

BACKGROUND OF THE INVENTION

This invention relates to suction devices for medical purposes, and in particular to a covered suction device with a retractable, protective sheath and with a closure secured to the sheath. The closure includes a cap which is automatically closed when the sheath is deployed.

Suction devices, for aspirating fluids from the body, are well known. Such suction devices typically include an elongated suction tube which is connectable at one end to a source of suction. The other end includes a tip having one or more holes leading to the suction tube to aid in aspiration as the suction device is being used.

The problem with prior suction devices is contamination. Suction devices are typically used over a period of time, and once first used, the device is contaminated. If the device is not protected in some manner, once it has been used, if it is laid aside for later use, it can further become contaminated by ambient contaminants, and transfer those contaminants to the patient the next time that it is used. Conversely, once it has been used on a sick patient, whatever ailment that is suffered by the patient can be passed from the suction device to whatever surface upon which it might be laid between uses, leading to contamination transferred from the patient to others. It is therefore important that the suction device be protected in some manner, both to protect the patient as well as others.

In the past, protection has been by means of providing a sterile surface upon which the suction device can be placed between uses. While that generally is satisfactory for largely eliminating passage of any contaminants from the patient, with the suction device being open to the ambient surroundings between uses, it still is subject to contamination by the surroundings, with that contamination then being passed back to the patient the next time that the suction device is used.

It is therefore important to provide a suction device which is both protected from passing contaminates from the patient to other patients and the surroundings, as well as being protected from passing ambient contamination back to the patient.

SUMMARY OF THE INVENTION

The invention is directed to a suction device comprising an elongated suction tube having opposite ends. A connector is located at one end of the suction tube, and a suction tip is located at the other end of the suction tube. A retractable, protective sheath surrounds at least a portion of the suction tube, with the sheath having one end secured to the suction tube and an opposite free end. A closure is secured to the free end, with a closure having a moveable cap. An automatic cap closer is associated with the cap to appropriately close the cap over the tip.

In accordance with the preferred form of the invention, the cap is pivotal, and the automatic cap closer comprises a manipulator for the cap. The manipulator preferably comprises a pivot wheel which extends about a pivot axis for the cap, with the cap being secured to the pivot wheel. Preferably the pivot wheel has a roughened outer surface to provide sufficient friction when the pivot wheel engages the suction tip.

In accordance with the preferred form of the invention, the suction tip includes an enlargement which is engageable by the pivot wheel. The enlargement preferably comprises an enlarged circumference of the suction tip which is greater than the circumference of the remaining portion of the suction tube.

The preferred form of the closure comprises a cylindrical body, with the cap being pivotally attached to one side of the cylindrical body at one end of the cylindrical body. The cylindrical body has an internal dimension which closely matches the circumference of the suction tip, both to provide a sufficient seal and also engage the pivot wheel when the sheath is deployed to cover the tip.

The connector can be formed in any well-known manner to connect to a source of suction. The connector can form part of a handle which includes a suction control. The suction control can be formed to be manipulated in order to control the amount of suction at the suction tip.

BRIEF DESCRIPTION OF THE DRAWING

The invention is described in greater detail in the following description of an example embodying the best mode of the invention, taken in conjunction with the drawing figures, in which:

FIG. 1 is a perspective view of a suction device according to the invention, with the protective sheath being deployed, FIG. 2 is a perspective view similar to that of FIG. 1, but with the protective sheath retracted, FIG. 3 is an enlarged perspective view of the closure when retracted as depicted in FIG. 2, with a portion cut away to illustrate detail, FIG. 4 is a perspective view of the tip of the suction device, with the closure deployed and the cap closed, FIG. 5 is an enlarged cross sectional view of the tip, showing the closure partially deployed toward the closed position and, FIG. 6 is an enlarged elevational illustration of the cap when retracted to the position shown in FIG. 2.

DESCRIPTION OF AN EXAMPLE EMBODYING THE BEST MODE OF THE INVENTION

A suction device according to the invention is shown generally at 10 in the drawing figures. The suction device 10 is composed of an elongated suction tube 12 terminated by a connector 14 at one end and a suction tip 16 at the other end. The connector 14 can be connected directly to the suction tube 12, or, as illustrated, the connector 14 can form part of a hollow grip 18 which is connected to the suction tube 12. That connection can be a permanent connection formed in an appropriate manner between the suction tube 12 and the grip 18, or can be a mechanical connection, such as a force fit or a snap fit. The manner of connection of the tube 12 to the grip 18 forms no part of the invention.

A retractable, protective sheath 20 surrounds at least a portion of the suction tube 12. The sheath 20 has one end which is appropriately secured to the grip 18, and an opposite free end to which a closure 22 is secured.

The suction tip 16 is enlarged, as illustrated, in the vicinity of the end of the suction tube 12. The enlarged portion can be formed of a soft plastic material to cushion the tip when used and is provided with an end aperture 24 and one or more radial apertures 26. Primary suction is through the end aperture 24, but if that aperture becomes clogged, suction can be through the radial apertures 26. Also, the radial apertures relieve suction if the end aperture is inadvertently pushed against tissue, effectively sealing the end aperture.

The closure 22 preferably comprises a cylindrical body, with opposite finger grips 28 to facilitate deployment of the protective sheath 20 over the suction tube 12. The sheath 20 is appropriately secured within the closure 22, such as by means of a ring 30 installed in the inner diameter of the closure 22. The ring 30 can be fixed in place, such as by an adhesive, by sonic welding, or the like, so long as the sheath 20 is fixed within the closure 22 to prevent inadvertent separation between the closure 22 and the sheath 20. Also, the ring 30 is sized to closely approximate the outer diameter of the enlarged suction tip 16, as desired.

A moveable cap 32 is positioned to be closed over one end of the cylindrical closure 22. The cap 32 can include one or more holes 34, as illustrated, so that an air-tight seal is not effected when the cap 32 is closed.

The cap 32 extends from a pivot wheel 36. The pivot wheel 36, which has a roughened outer surface 38, includes an integral axle pin 40 snapped into opposite brackets 42 and 44 extending outwardly from the closure 22. The closure 22 can be formed of plastic, with the brackets 42 and 44 molded thereon. The cap 32, pivot wheel 36 and axle 40 can also be a single molded plastic part.

The pivot wheel 36 has a sufficient diameter so that, as best illustrated in FIG. 5, when the enlarged suction tip 16 is encountered, the roughened outer surface 38 engages the suction tip 16, causing the closure 32 to either open or close, depending on the direction of movement of the closure 22 relative to the suction tip 16. Thus, the cap 32 is automatically closed by engagement of the pivot wheel 36 on the enlarged suction tip 16, as the cylindrical closure 22 is extended over the tip 16, or it is automatically opened by movement in the opposite direction.

The protective sheath 20 is preferably formed of a pliable plastic material which can be readily gathered as the closure 22 is retracted from the tip 16. Thus, as best illustrated in FIG. 3, when the closure 22 is fully retracted, the sheath 20 is gathered in a bell-shaped housing portion of the closure 22. Therefore, when the sheath 20 is retracted to expose the suction tube 12 and the suction tip 16, the sheath 20 is neatly gathered beneath the closure 22, both protecting the sheath 20 from an inadvertent tear, as well as keeping it out of the way when the suction device 10 is used.

Other means of gathering the sheath when the closure 22 is retracted will be apparent to one skilled in the art. While having the bell-shaped housing portion of the closure 22 is preferred, having a gathering means separate from the closure can also be employed.

The grip 18 can include a suction control 46 so that the user of the suction device 10 can control the amount of suction available at the tip 16. The control 46 can comprise any well-known means of controlling fluid flow through the suction tube 12.

In use, the suction device 10 is normally provided as illustrated in FIG. 1, with the protective sheath 20 fully deployed with the closure 22 about the suction tip 16 and the cap 32 closed thereover. The connector 14 is then connected to an appropriate source of suction (not illustrated).

When the suction device is to be used to aspirate fluids, the user simply grips the closure 22 at the finger grips 28. The user then retracts the closure 22, which automatically opens the cap 32 as illustrated in FIG. 5. Alternatively, the rising tip 16 can push against the underside of the cap 32, opening the cap in this manner. The closure 22 is then fully retracted to the position shown in FIG. 2, with the protective sheath 20 gathered within the lower bell housing of the closure 22 as illustrated in FIG. 3. The suction device 10 can then be used, and after use, the closure 22 is simply returned along the suction tube 12 to the suction tip 16, where the pivot wheel 36 engages the enlarged suction tip 16, automatically closing the cap 32 to the position shown in FIG. 4. In this manner, the suction device 10 can be used and reused, protecting the tube 12 and tip 16 from either passing contamination to the ambient surroundings, or receiving contamination from the surroundings. The suction device 10 thus provides an effective means of avoiding contamination during use of the suction device 10. Thereafter, the suction device 10 can be preferably discarded, or, in some instances, it can be cleaned and reused.

Various changes can be made to the invention without departing from the spirit thereof or scope of the following claims.

What is claimed is:

1. A suction device comprising:
   a. an elongated suction tube having opposite ends,
   b. a connector at one end of said suction tube,
   c. a suction tip at the other end of said suction tube,
   d. a retractable, protective sheath surrounding at least a portion of said suction tube, said sheath having one end secured to said suction tube and an opposite free end,
   e. a closure secured to said free end, said closure having a movable cap, and
   f. an automatic cap closer associated with said cap and engagable with said suction tip to close said cap.

2. The suction device according to claim 1 in which said cap is pivotal, and said automatic cap closer comprises a manipulator for said cap.

3. The suction device according to claim 2 in which said manipulator comprises a pivot wheel extending about a pivot axis for said cap, said cap being secured to said pivot wheel.

4. The suction device according to claim 3 in which said pivot wheel has a roughened outer surface engageable with said suction tip.

5. The suction device according to claim 4 in which said suction tip includes an enlargement engageable by said pivot wheel.

6. The suction device according to claim 5 in which said enlargement comprises an enlarged circumference of said suction tip.

7. The suction device according to claim 1 in which said closure includes a cylindrical body, said cap being pivotally attached to one side of said cylindrical body at one end thereof.

8. The suction device according to claim 1 including a suction control.

9. The suction device according to claim 8 in which said suction control is proximate said one end.

10. A suction device comprising
    a. an elongated suction tube having opposite ends,
    b. a connector at one end of said suction tube,
    c. a suction tip at the other end of said suction tube,
    d. a retractable, protective sheath surrounding at least a portion of said suction tube, said sheath having one end secured to said suction tube and an opposite free end,
    e. a cylindrical closure secured to said free end, said closure having a movable cap, and
    f. means engagable with said suction tip for pivoting said cap from an open position to a closed position when said closure is moved relative to said suction tip at said suction tip.

11. The suction device according to claim 10 in which said suction tip includes an enlargement, and said pivoting means comprising an axis at one side of said closure and a pivot wheel mounted on said axis, said cap being secured to said pivot wheel and said pivot wheel engaging said enlargement when said closure is moved relative to said suction tip.

12. The suction device according to claim 11 in which said enlargement comprises an enlarged circumference of said suction tip.

13. The suction device according to claim 10 including a suction control.

14. A section device comprising:
   a. an elongated suction tube having opposite ends,
   b. a connector at one end of said suction tube,
   c. a suction tip at the other end of said suction tube,
   d. a retractable, protective sheath surrounding at least a portion of said suction tube, said sheath having one end secured to said suction tube and an opposite free end,
   e. a cylindrical closure secured to said free end, said closure having a movable cap and said sheath having a length such that said closure can be positioned with said suction tip within said closure, and
   f. an automatic cap closer attached to a distal end of said closure, said cap closer being engagable with said suction tip to close said cap.

15. The suction device according to claim 14 in which said suction tip includes an enlargement, and said automatic cap closer comprises a pivot wheel extending about a pivot axis for said cap, said cap being secured to said pivot wheel and said pivot wheel being engageable with said enlargement.

16. The suction device according to claim 15 in which said pivot wheel has a roughened outer surface.

17. The suction device according to claim 15 in which said enlargement comprises an enlarged circumference of said suction tip.

18. A suction device comprising:
   a. an elongated suction tube having opposite ends,
   b. a retractable, protective sheath surrounding at least a portion of said suction tube, said sheath having one end secured to said suction tube and an opposite free end,
   c. a closure secured to said free end, and
   d. means for gathering said sheath when said sheath is retracted, said gathering means comprising a bell-shaped housing portion of said closure.

19. The suction device according to claim 18, including a closure secured to said free end, said closure having a pivotal cap and an automatic cap closer associated with said cap, said automatic closure comprising a manipulator engagable with said suction tip to close said cap.

20. The suction device according to claim 19 in which said manipulator comprises a pivot wheel extending about a pivot axis for said cap, said cap being secured to said pivot wheel.

* * * * *